(12) United States Patent
Holman et al.

(10) Patent No.: US 8,672,990 B2
(45) Date of Patent: Mar. 18, 2014

(54) FIBER MESH CONTROLLED EXPANSION BALLOON CATHETER

(75) Inventors: Thomas J. Holman, Princeton, MN (US); Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1262 days.

(21) Appl. No.: 11/139,253

(22) Filed: May 27, 2005

(65) Prior Publication Data
US 2006/0271093 A1   Nov. 30, 2006

(51) Int. Cl.
*A61F 2/06*   (2013.01)

(52) U.S. Cl.
USPC ........................................... 623/1.11

(58) Field of Classification Search
USPC .................. 623/1.11, 1.32, 1.12; 604/101.1, 604/101.05, 103.05, 103.08, 103.07, 604/103.09, 103.12, 96.01, 104, 22; 606/192, 193, 194, 159, 108, 200
See application file for complete search history.

(56) References Cited

U.S. PATENT DOCUMENTS

| | | | |
|---|---|---|---|
| 2,701,559 A | 2/1955 | Cooper | |
| 2,854,983 A * | 10/1958 | Baskin | 604/103.11 |
| 3,509,883 A | 5/1970 | Dibelius | 128/348 |
| 3,996,938 A | 12/1976 | Clark, III | 128/348 |
| 4,327,736 A | 5/1982 | Inoue | 128/349 |
| 4,572,186 A | 2/1986 | Gould et al. | 128/341 |
| 4,637,396 A | 1/1987 | Cook | 128/344 |
| 4,650,466 A * | 3/1987 | Luther | 604/95.04 |
| 4,702,252 A | 10/1987 | Brooks et al. | 128/344 |
| 4,706,670 A | 11/1987 | Anderson et al. | 606/195 |
| 4,723,549 A * | 2/1988 | Wholey et al. | 606/194 |
| 4,793,348 A * | 12/1988 | Palmaz | 606/194 |
| 4,796,629 A | 1/1989 | Grayzel | 128/344 |
| 4,885,003 A * | 12/1989 | Hillstead | 604/22 |
| 4,921,484 A * | 5/1990 | Hillstead | 604/104 |
| 4,983,167 A | 1/1991 | Sahota | 606/194 |
| 5,002,560 A * | 3/1991 | Machold et al. | 606/198 |
| 5,116,318 A * | 5/1992 | Hillstead | 604/103.14 |
| 5,156,785 A | 10/1992 | Zdrahala | 264/108 |
| 5,171,297 A | 12/1992 | Barlow et al. | 604/96 |
| 5,195,969 A | 3/1993 | Wang et al. | 604/96.01 |
| 5,211,654 A | 5/1993 | Kaltenbach | 606/191 |
| 5,221,261 A * | 6/1993 | Termin et al. | 604/104 |
| 5,248,305 A | 9/1993 | Zdrahala | 604/280 |

(Continued)

FOREIGN PATENT DOCUMENTS

EP   0 872 253 A2   10/1998
WO   98/05377   2/1998

OTHER PUBLICATIONS

U.S. Appl. No. 10/849,742, filed May 20, 2004, Hom.
U.S. Appl. No. 10/862,250, filed Jun. 7, 2004, Mapes, et al.

(Continued)

*Primary Examiner* — Victor Nguyen
*Assistant Examiner* — Jocelin Tanner
(74) *Attorney, Agent, or Firm* — Vidas, Arrett & Steinkraus

(57) ABSTRACT

A medical device having a catheter shaft having a distal portion and a proximal portion, a medical balloon co-axially mounted on the distal portion of the catheter shaft and a tubular mesh wrapped around the balloon, wherein the mesh strengthens and reinforced the balloon and may be manipulation to dictate the shape of the balloon and to squeeze the balloon down onto the catheter shaft during deflation of the balloon.

24 Claims, 28 Drawing Sheets

(56) References Cited

U.S. PATENT DOCUMENTS

| | | | | |
|---|---|---|---|---|
| 5,250,070 | A | 10/1993 | Parodi | 606/194 |
| 5,270,086 | A | 12/1993 | Hamlin | 428/35.2 |
| 5,295,959 | A * | 3/1994 | Gurbel et al. | 604/103.13 |
| 5,330,429 | A | 7/1994 | Noguchi | 604/96 |
| 5,338,299 | A | 8/1994 | Barlow | 604/96 |
| 5,492,532 | A * | 2/1996 | Ryan et al. | 604/103.09 |
| 5,534,007 | A | 7/1996 | St. Germain et al. | 606/108 |
| 5,558,642 | A * | 9/1996 | Harrison et al. | 604/103.01 |
| 5,587,125 | A | 12/1996 | Roychowdhury | 264/515 |
| 5,620,649 | A | 4/1997 | Trotta | 264/515 |
| 5,647,848 | A | 7/1997 | Joergensen | 604/103.11 |
| 5,693,014 | A | 12/1997 | Abele et al. | 604/103.08 |
| 5,702,410 | A * | 12/1997 | Klunder et al. | 606/194 |
| 5,718,684 | A * | 2/1998 | Gupta | 604/103.07 |
| 5,766,203 | A * | 6/1998 | Imran et al. | 623/1.11 |
| 5,772,681 | A | 6/1998 | Leoni | 606/192 |
| 5,820,613 | A | 10/1998 | Van Werven-Franssen et al. | 604/282 |
| 5,833,657 | A | 11/1998 | Reinhardt et al. | 604/96 |
| 5,868,704 | A | 2/1999 | Campbell et al. | 604/96 |
| 5,868,708 | A | 2/1999 | Hart et al. | 604/104 |
| 5,868,779 | A * | 2/1999 | Ruiz | 606/194 |
| 5,879,369 | A | 3/1999 | Ishida | 606/94 |
| 5,911,702 | A | 6/1999 | Romley et al. | 604/53 |
| 5,972,019 | A * | 10/1999 | Engelson et al. | 606/200 |
| 6,004,289 | A | 12/1999 | Saab | 604/96 |
| 6,013,093 | A * | 1/2000 | Nott et al. | 606/200 |
| 6,036,697 | A | 3/2000 | DiCaprio | 606/108 |
| 6,059,751 | A | 5/2000 | Ostapchenko et al. | 604/96 |
| 6,068,610 | A * | 5/2000 | Ellis et al. | 604/96.01 |
| 6,123,718 | A | 9/2000 | Tu et al. | 606/198 |
| 6,124,007 | A | 9/2000 | Wang et al. | 428/35.2 |
| 6,143,015 | A | 11/2000 | Nobles | 606/194 |
| 6,156,254 | A | 12/2000 | Andrews et al. | 264/231 |
| 6,242,063 | B1 | 6/2001 | Ferrera et al. | 428/35.2 |
| 6,248,121 | B1 | 6/2001 | Nobles | 606/194 |
| 6,325,780 | B1 | 12/2001 | Schaible et al. | 604/103.06 |
| 6,416,459 | B1 * | 7/2002 | Haindl | 600/37 |
| 6,450,989 | B2 * | 9/2002 | Dubrul et al. | 604/104 |
| 6,530,938 | B1 | 3/2003 | Lee et al. | 606/194 |
| 6,554,795 | B2 | 4/2003 | Bagaoisan | 604/103.11 |
| 6,585,688 | B2 | 7/2003 | Ferrera et al. | 604/96.01 |
| 6,626,861 | B1 * | 9/2003 | Hart et al. | 604/96.01 |
| 6,663,660 | B2 | 12/2003 | Dusbabek et al. | 623/1.11 |
| 6,695,809 | B1 | 2/2004 | Lee | 604/96.01 |
| 6,733,474 | B2 * | 5/2004 | Kusleika | 604/103.01 |
| 6,746,424 | B2 | 6/2004 | Stamberg | 604/103.06 |
| 6,746,425 | B1 | 6/2004 | Beckham | 604/103.09 |
| 6,818,006 | B2 * | 11/2004 | Douk et al. | 606/200 |
| 7,156,860 | B2 * | 1/2007 | Wallsten | 606/192 |
| 2001/0043998 | A1 | 11/2001 | Chen | 428/35.7 |
| 2002/0010489 | A1 | 1/2002 | Grayzel et al. | 606/194 |
| 2002/0098307 | A1 | 7/2002 | Schwartz et al. | 428/36.3 |
| 2002/0161388 | A1 | 10/2002 | Samuels | |
| 2002/0193820 | A1 | 12/2002 | Wakuda | |
| 2003/0143350 | A1 | 7/2003 | Jimenez | 428/35.2 |
| 2004/0082965 | A1 | 4/2004 | Beckham | 606/192 |
| 2004/0098021 | A1 | 5/2004 | Laguna | 606/194 |
| 2004/0101644 | A1 | 5/2004 | Kinoshita et al. | 428/35.7 |
| 2004/0109964 | A1 | 6/2004 | Beckham | 428/35.9 |
| 2004/0126526 | A1 | 7/2004 | Parsonage et al. | 428/36.91 |
| 2006/0229645 | A1 * | 10/2006 | Bonnette et al. | 606/159 |

OTHER PUBLICATIONS

U.S. Appl. No. 10/889,574, filed Jul. 7, 2004, Schewe, et al.

* cited by examiner

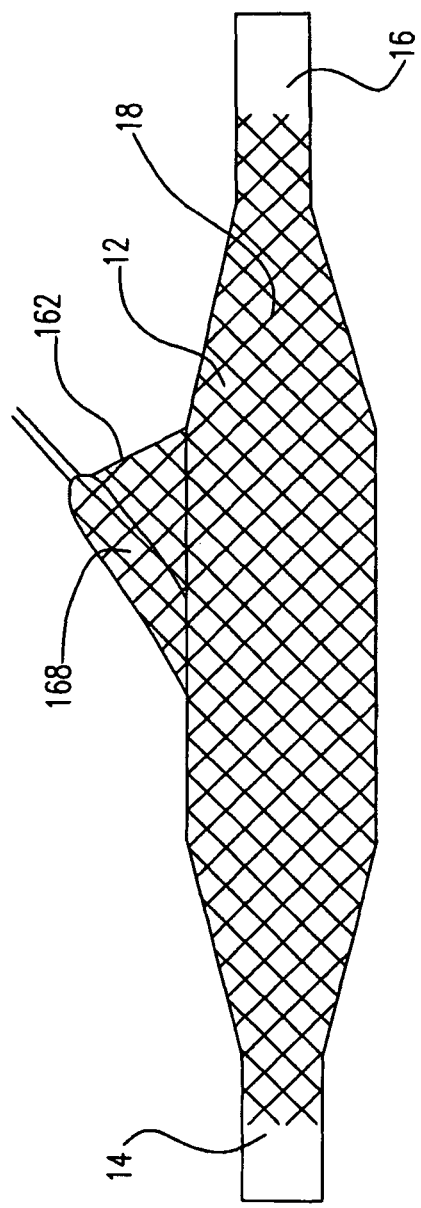

FIBER MESH CONTROLLED EXPANSION BALLOON CATHETER

BACKGROUND OF THE INVENTION

1. Field of the Invention

This invention relates to the field of balloon catheters. More specifically, the invention relates to catheter balloon and fiber mesh combinations and their methods of use.

2. Description of the Related Art

Percutaneous transluminal angioplasty (PTA) is a procedure, including ercutaneous transluminal coronary angioplasty (PTCA), which is well established for the treatment of blockages, lesions, stenosis, thrombus, etc. present in body lumens, such as the coronary arteries and/or other vessels.

Percutaneous angioplasty makes use of a dilatation balloon catheter, which is introduced into and advanced through a lumen or body vessel until the distal end thereof is at a desired location in the vasculature. Once in position across an afflicted site, the expandable portion of the catheter, or balloon, is inflated to a predetermined size with a fluid at relatively high pressures. By doing so the vessel is dilated, thereby radially compressing the atherosclerotic plaque of any lesion present against the inside of the artery wall, and/or otherwise treating the afflicted area of the vessel. The balloon is then deflated to a small profile so that the dilatation catheter may be withdrawn from the patient's vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, such as a stent, inside the artery at the lesion.

Catheter balloons are exposed to large amounts of pressure. Additionally, the profile of balloons must be small in order to be introduced into blood vessels and other small areas of the body. Therefore, materials with high strength relative to film thickness are chosen. These balloons require the requisite strength to withstand the pressure used for transit in a blood vessel and expansion to open an occluded vessel and the ability not to expand beyond a predetermined size and to maintain substantially a profile so as not to rupture or dissect the vessel as the balloon expands.

The requirements for the strength and size of the balloon vary widely depending on the balloon's intended use and the vessel size into which the catheter is inserted.

Areas of concern in balloon and balloon catheter development include hoop strength, molecular orientation, material selection, thermal processing, profile, burst strength, pressure capabilities, catheter trackability and pushability and plastic deformation, as well as others. These and other issues are addressed by the present invention to enhance product performance and to minimize the possibility of patient trauma and recovery.

All US patents, applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention is directed to a variety of embodiments. For example, in at least one embodiment the invention is directed to a balloon catheter, wherein a mesh is wrapped about at least part of the balloon. In one particular embodiment, one end of the mesh is fixed in place relative to the catheter shaft, while the other end is connected to an elastic restraining mechanism. As the balloon is expanded, the mesh and elastic restraining mechanism resist the radial expansion of the balloon. After the internal pressure is relieved, the mesh, under the pulling force of the elastic restraining mechanism, draws the balloon down to a reduced profile.

In a further embodiment, the mesh may be proximately restrained via a loadable spring. In this particular embodiment, the proximal end of the mesh is connected to the distal end of a spring, which is coaxially mounted on the catheter shaft. As the balloon is expanded, a load is built up in the spring. Upon reduction of balloon pressure, the spring pulls the mesh proximally, thus drawing the mesh down over the balloon.

In at least one embodiment, a restraining strip longitudinally extends across the balloon and may be embedded in or attached to the mesh. The strip is connected to proximal and distal retaining rings, which are mounted on the catheter shaft on either side of the balloon. As the balloon is expanded, lobes are created as the balloon expands on either side of the strip. Upon the reduction of balloon pressure, the balloon is drawn down under the restraining force of the mesh/strip combination.

In a further embodiment, a manual restraining mechanism is configured such that the user may apply a pulling force on the mesh from the manifold. Upon the reduction of balloon pressure, the user may draw the mesh proximally via pull wire, thus reducing the profile of the balloon.

In at least one embodiment, the mesh, which is mounted about the balloon, has a plurality of crossing strands forming the mesh. Pre-selected crossing strands are fused or bonded together, such that they remain fixed relative to one another at the point of the bond. The remaining crossing strands are allowed to move freely across one another with the movement of the balloon and mesh combination. By pre-selecting a specific pattern of bonded strands, one may control and create a specific expansion shape of the balloon. In particular, fusing the junctures that, when the balloon is inflated, lie in annular regions at or near to the transition from balloon waist-to-cone or cone-to-body, while leaving the major proportion of the junctures over at least the body region unfused, facilitates proper alignment of the mesh over the balloon during inflation and allows a highly efficient collapse of the mesh and balloon to a reduced profile after inflation.

These and other embodiments, which characterize the invention, are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

FIG. 28 is a side view of an embodiment of the mesh of the present invention mounted on a balloon.

DETAILED DESCRIPTION OF THE INVENTION

Figure 1:
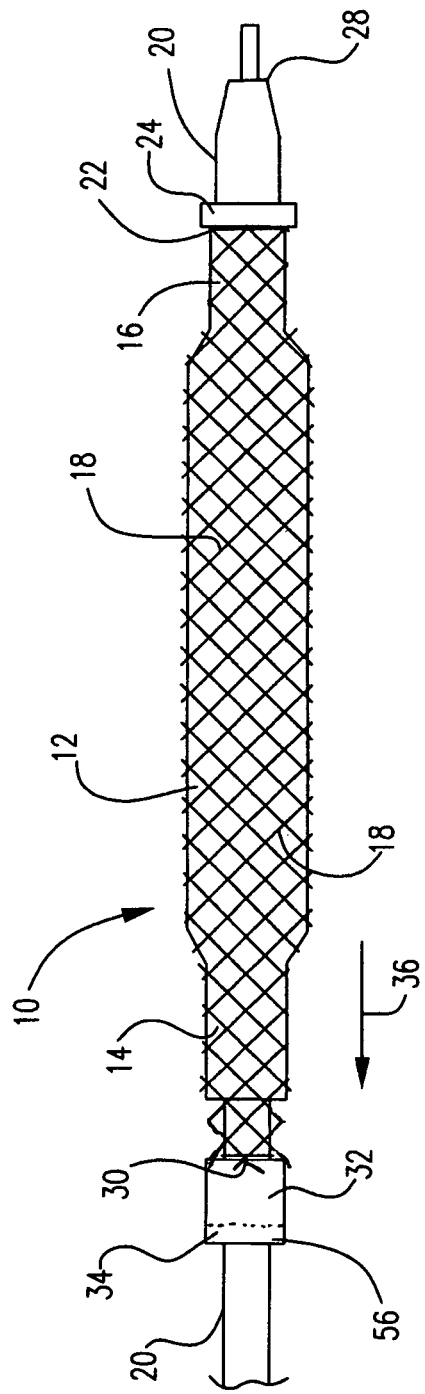
FIG. 1 is a side perspective view of the distal portion of an embodiment of the invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 2:
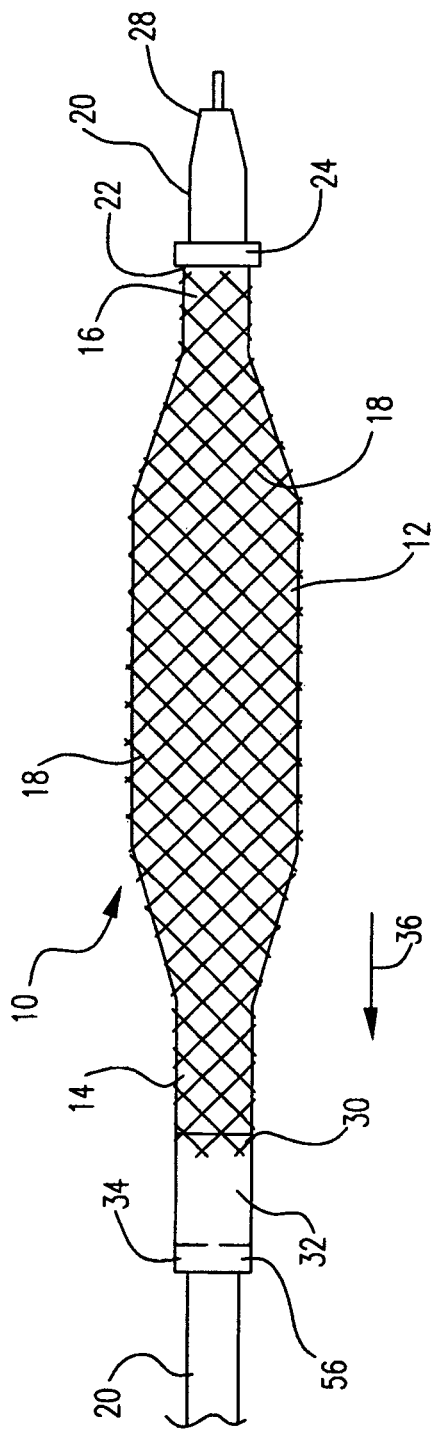
FIG. 2 is a side perspective view of the distal portion of an embodiment of the invention.

In at least one embodiment, an example of which is shown in FIGS. 1-2, the distal end of a catheter system 10 is depicted, which includes a catheter shaft 20 and a balloon 12 mounted thereon. The balloon 12 has a proximal waist 14 and a distal waist 16, both of which are connected to the catheter shaft 20. The balloon 12 may be expandable via conventional means. FIG. 1 illustrates the balloon 12 in its contracted state and FIG. 2 illustrates the balloon 12 in its expanded state.

The embodiment further includes a mesh 18, which is positioned about the balloon 12. The mesh 18 is in tubular form and is free-floating over the outer surface of the balloon 12, which means that it is not embedded in the balloon material and the mesh 18 and balloon 12 can move relative to each other as the balloon is inflated and deflated. The mesh 18 may be placed over the entire balloon or over part of it. In the particular embodiment shown in FIGS. 1-2, the distal end 22 of the mesh 18 is fixed in place relative to the catheter shaft 20. This may be achieved in any conventional manner. In the embodiment shown, the distal end 22 of the mesh 18 is held down on the catheter shaft 20 via a ring 24. The ring 24 may be positioned over the distal waist 16 of the balloon 12 or at a position distal to the distal waist 16. It should be understood that the mesh 18 may extend to the distal end 28 of the catheter.

As shown in FIGS. 1-2, in at least one embodiment, the proximal end 30 of the mesh 18 is attached to a tube 32, the proximal end 56 of which is connected to the catheter shaft 20 at point 34, via conventional methods, such as, but not limited to, adhesion and welding, etc. The tube 32 acts as a loadable restraining mechanism. In the embodiment shown, the tube 32 is an elastic tube, whereby a longitudinal pulling or biasing tension is applied to the mesh 18 in a direction shown by arrow 36. Suitable materials for the elastic tube include, but are not limited to, a rubber-like material, such as silicon rubber, latex, polyurethane, PVC, etc.

As the balloon is expanded, as shown in FIG. 2, the expansion forces of the inflated balloon axially pull the elastic tube 32, thus stretching it distally. Due to the greater diameter of the balloon 12 as it expands and contracts from an expanded state, a slight radial force is also created. When the pressure used in expanding the balloon 12 is reduced, the mesh 18 is drawn proximally by the elastic tension of the tube 32.

Figure 3:
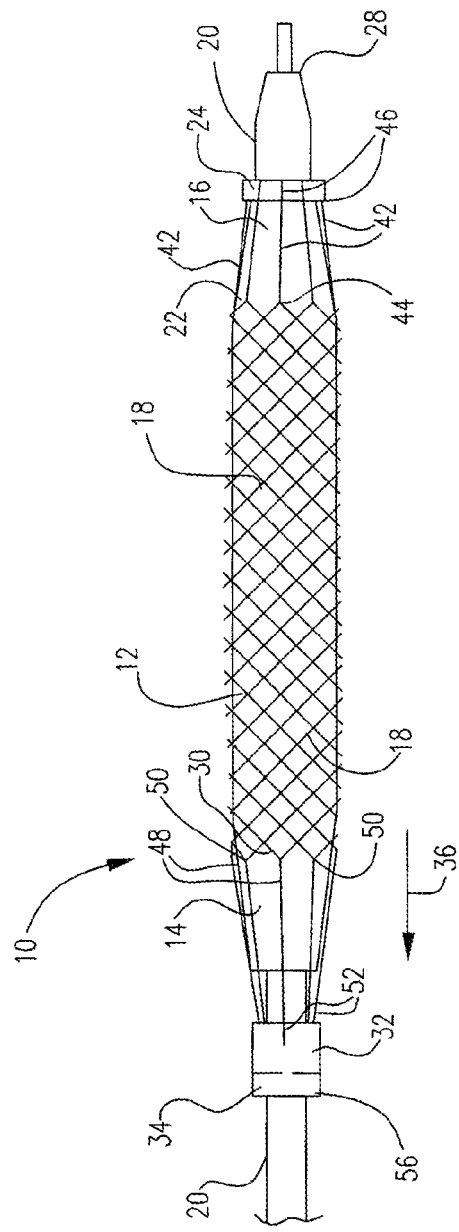
FIG. 3 is a side perspective view of the distal portion of an embodiment of the invention.
Figure 4:
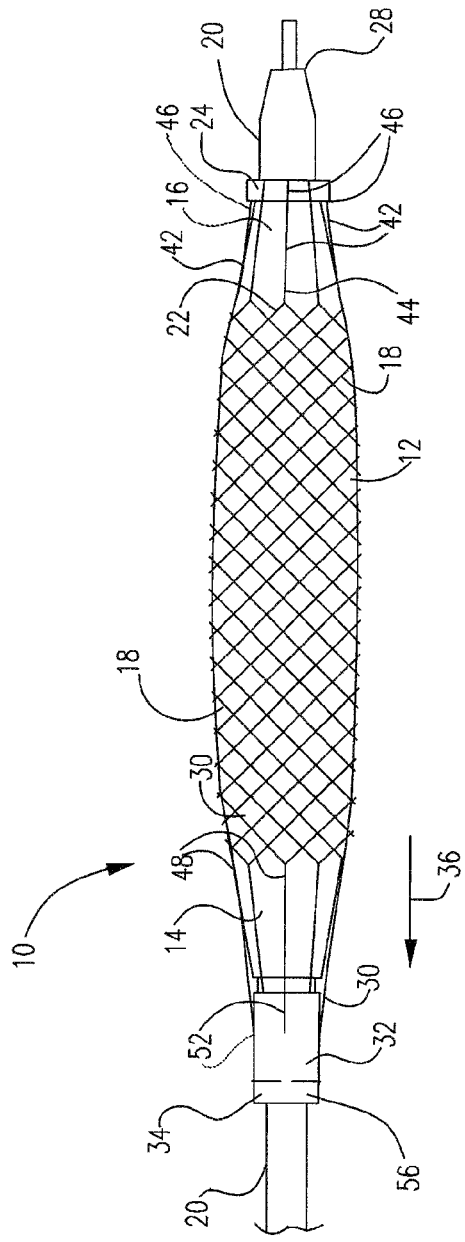
FIG. 4 is a side perspective view of the distal portion of an embodiment of the invention.

In at least a further embodiment, as shown in FIGS. 3-4, the mesh 18 may have a shorter length and cover less of the balloon 12. FIG. 3 illustrates the balloon 12 in its contracted state and FIG. 4 illustrates the balloon 12 in its expanded state. The distal end 22 of the mesh 18 is fixed in place relative to the catheter shaft 20 via a plurality of strands 42. The proximal ends 44 of the strands 42 are connected to the distal end 22 of the mesh 18. The distal ends 46 of the strands 42 are in turn connected to ring 24. The ring 24 may be positioned over the distal waist 16 of the balloon 12 or at a position distal to the distal waist 16. It should be understood that the strands 42 may also be directly connected to the balloon waist 16 or the catheter shaft 20. It should also be understood that strands 42, as well as strands 48 discussed below, may be a continuation of the mesh material, i.e., unwoven tails of the mesh.

As shown in FIGS. 3-4, in at least one embodiment, the proximal end 30 of the mesh 18 is connected to a second set of strands 48. The distal ends 50 of the strands 48 are connected to the proximal end 30 of the mesh 18. The proximal ends 52 of the strands 48 are in turn connected to tube 32, which is connected to the catheter shaft 20 at point 34.

As mentioned above, the tube 32 may be elastic, such that a pulling tension is applied to the strands 48, and thus the mesh 18, in a direction shown by arrow 36. As the balloon is expanded, as shown in FIG. 4, the expansion forces of the inflated balloon longitudinally overpower the elastic tube 32, thus stretching it distally. When the fluid pressure used in expanding the balloon is reduced, the mesh 18 is drawn proximally by the elastic tension of the tube 32, thus reducing the profile of the balloon 12. The invention also contemplates the embodiments discussed herein without a restraining mechanism, such as the tube 32, spring 58, etc., wherein the proximal end of the mesh 18 is secured directly to the catheter shaft 20.

Figure 5:
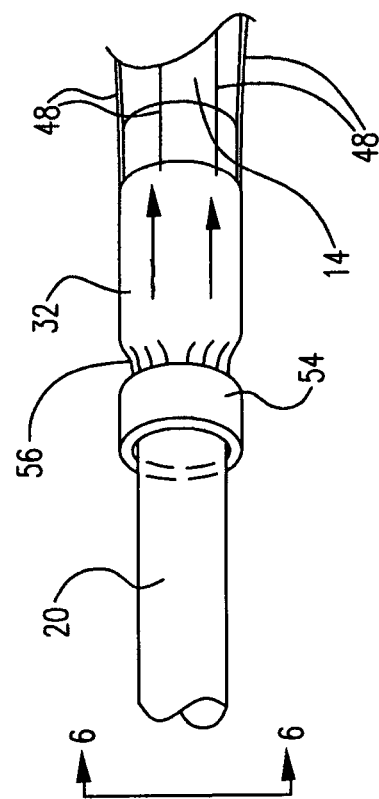
FIG. 5 is a partial side perspective view of the distal portion of an embodiment of the invention.
Figure 6:
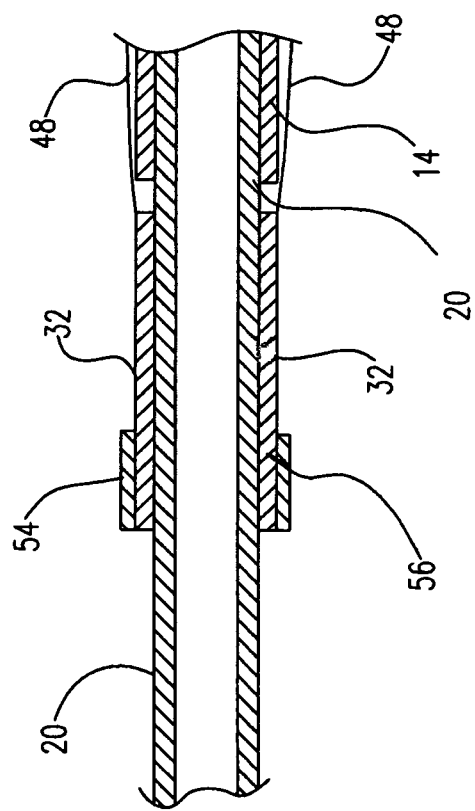
FIG. 6 is a cross-sectional view of the embodiment shown in FIG. 5 along lines 5-5.

As shown in FIG. 5, which is a partial perspective view, the proximal end 56 of the tube 32 may be held in place relative to the catheter shaft 20 by a crimping ring 54. FIG. 6 illustrates a cross-section view of FIG. 5 along lines 6-6.

Figure 7:
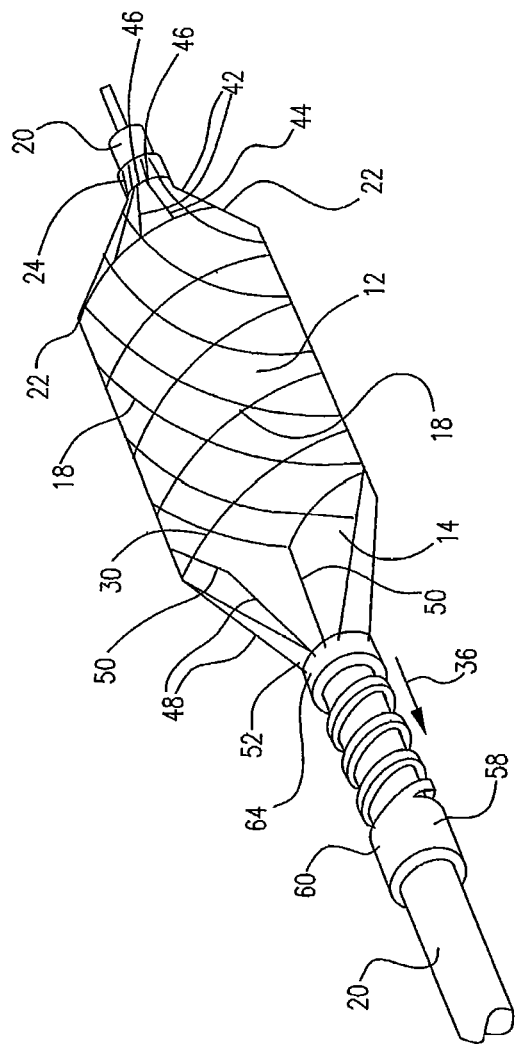
FIG. 7 is a side perspective view of the distal portion of an embodiment of the invention.
Figure 8:
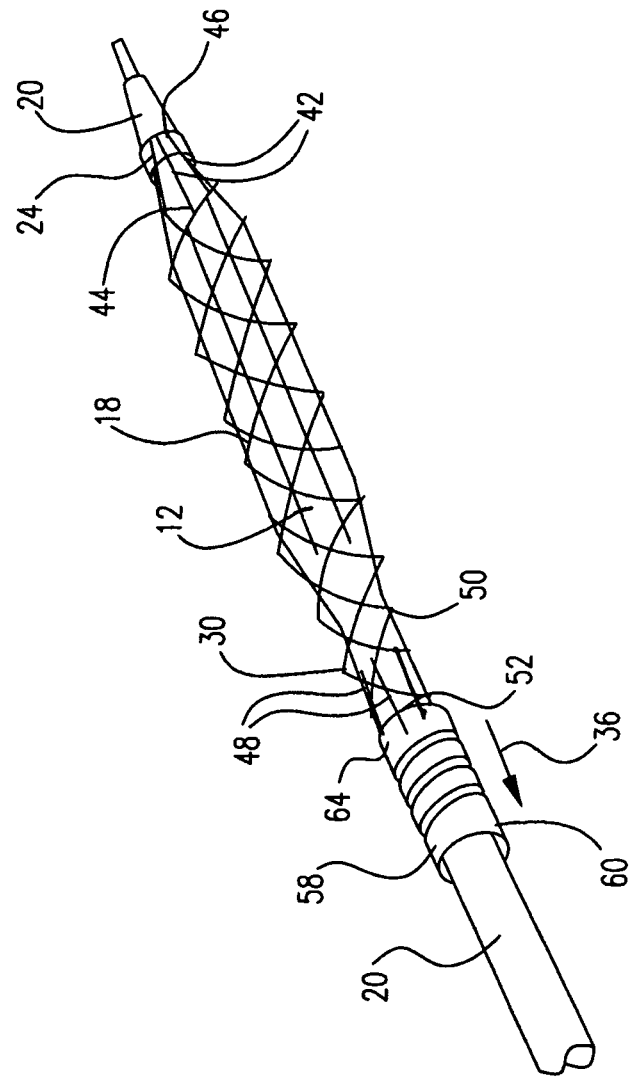
FIG. 8 is a side perspective view of the distal portion of an embodiment of the invention.
Figure 9:
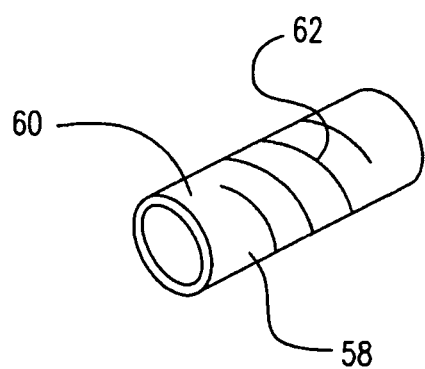
FIG. 9 is a side perspective view of a spring used in an embodiment of the invention.

FIGS. 7-9 illustrate a further embodiment of the invention. In this particular embodiment, the loadable restraining mechanism is a spring 58. FIG. 8 illustrates the balloon 12 in its contracted state and FIG. 7 illustrates the balloon 12 in its expanded state. The distal end 22 of the mesh 18 is fixed in place relative to the catheter shaft 20 via a plurality of strands 42. The proximal ends 44 of the strands 42 are connected to the distal end 22 of the mesh 18. The distal ends 46 of the strands 42 are in turn connected to ring 24. The ring 24 may be positioned over the distal waist 16 of the balloon 12 or at a position distal to the distal waist 16. It should be understood that the strands 42 may also be directly connected to the balloon waist 16 or the catheter shaft 20.

As shown in FIGS. 7-8, in at least one embodiment, the proximal end 30 of the mesh 18 is connected to a second set of strands 48. The distal ends 50 of the strands 48 are connected to the proximal end 30 of the mesh 18. The proximal ends 52 of the strands 48 are in turn connected to spring 58, which is connected to the catheter shaft 20. It should be understood that the spring 58 may be directly connected to the mesh 18.

As mentioned above, the spring 58 may be loaded, such that a pulling tension is applied to the strands 48, and thus the mesh 18, in a direction shown by arrow 36. As the balloon is expanded, as shown in FIG. 7, the expansion forces of the inflated balloon longitudinally overpower the spring 58, thus stretching it distally. When the pressure used in expanding the balloon is reduced, the mesh 18 is drawn proximally by the elastic tension of the spring 58.

Spring 58 may be made by any conventional means, including, but not limited to, shaping a coil from a piece of suitable material or mechanical or laser cutting 62 a coiled shape into a tube of suitable material, as shown in FIG. 9. Other patterns which allow elongation of the spring 58 upon application of a pulling force may be used, including, but not limited to, horizontal "S" shape cuts along the axis. The spring 58 may be made from suitable materials, such as, but not limited to, plastic, stainless steel, nitinol and titanium.

The proximal end 60 of the spring 58 may be held in place relative to the catheter shaft 20 by suitable means, such as, but not limited to, adhesion, welding or by a restraining ring, etc. The distal end 64 is allowed slide over the catheter shaft 20 as the balloon 12 expands and contracts.

Figure 10:
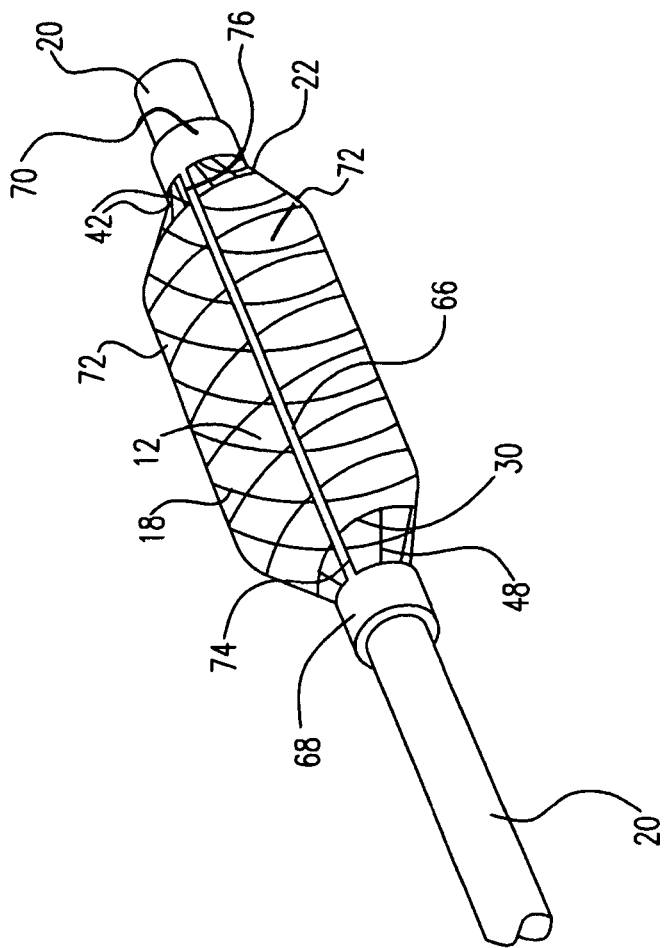
FIG. 10 is a side perspective view of the distal portion of an embodiment of the invention.
Figure 11:
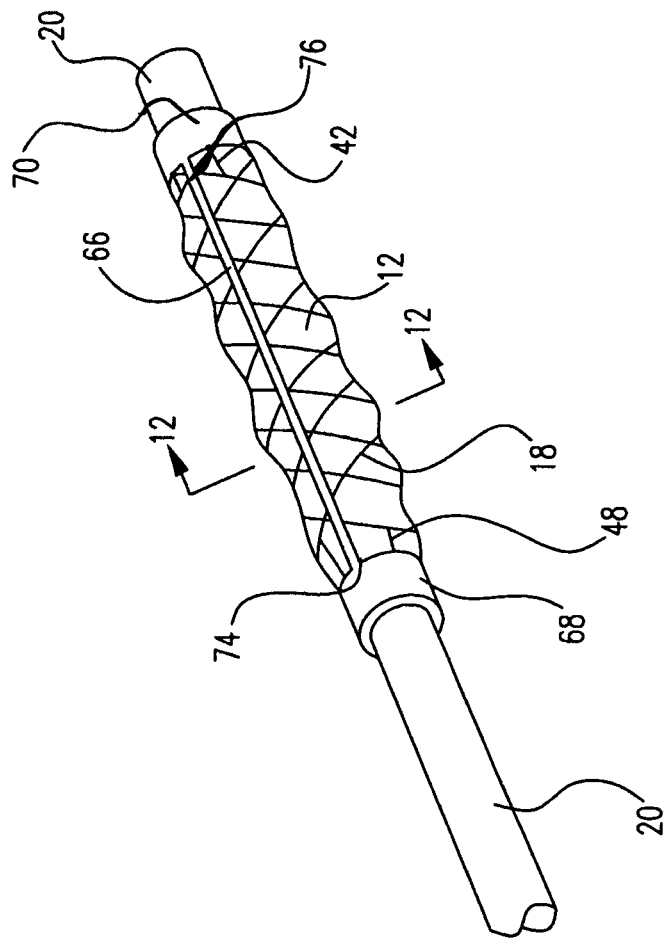
FIG. 11 is a side perspective view of the distal portion of an embodiment of the invention.
Figure 12:
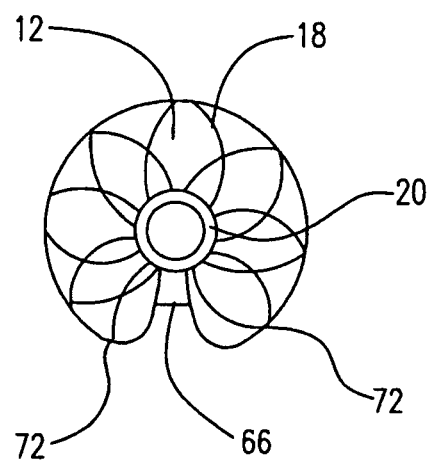
FIG. 12 is a cross-sectional view of the embodiment shown in FIG. 11 along lines 12-12.

FIGS. 10-12 illustrate a further embodiment of the invention. In this particular embodiment, the loadable restraining mechanism is a strip 66 longitudinally extending across the mesh 18 and balloon 12. The strip 66 is connected to, or integral with, proximal ring 68 and distal ring 70, which are both connected to the catheter shaft 20. The strip 66 may also be embedded in or connected to the mesh 18. In this particular embodiment, lobes 72 are formed due to the restraint created by the strip 66. FIG. 11 illustrates the balloon 12 in its contracted state and FIG. 10 illustrates the balloon 12 in its expanded state. FIG. 12 illustrates a cross-section of the embodiment shown in FIG. 11 along lines 12-12.

The distal ring 70 and proximal ring 68 shown in FIGS. 10-11 are connected to the catheter shaft 20. It should be understood that rings 68 and 70 may take the form of a partial rings and may be fixed in place relative to the catheter shaft 20 or may be slidably connected to the catheter shaft 20.

The proximal end 74 of the strip 66 is connected to the proximal ring 68 and the distal end 76 of the strip 66 is connected to the distal ring 70. The strip 66 may be integral with the rings 68, 70, or may be a separate piece which is connected to the rings 68, 70, by suitable means, such as, but not limited to, adhesion or welding. The strip 66 may have elastic characteristics, such that, when the balloon is expanded, it stretches under force of the expanding balloon 12. The tension created by the strip 66 causes the formation of lobes 72 in the balloon 12. When the pressure is relieved, the strip 66 draws the mesh 18 down, which in turn draws the balloon 12 down to reduce the profile of the catheter.

In one particular embodiment, the strands of the mesh 48, 42, are connected to ring 68 and ring 70, respectively. It should also be understood that the ends of the mesh 30, 22, may also be directly connected to the rings 68, 70. One or both of the rings 68, 70, are slidable along the catheter shaft 20. As the balloon 12 expands, the strip 66 bends and the rings 68, 70, slide closer together, allowing the mesh 18 under the strip 66 to foreshorten. When the pressure is released, the strip 66 straightens, forcing the rings 68, 70, apart, which, in turn, draws the mesh 18 down to reduce the profile of the balloon 12. In this particular embodiment, the strip 66 is thin enough to be flexible so that is may bend with the balloon 12, but inelastic enough to push the rings 68, 70, apart during depressurizing. The strip 66 may be made from suitable materials, such as, but not limited to, plastic, stainless steel, nitinol and titanium.

It should be understood that the invention contemplates two or more strips 66 spaced circumferentially around the balloon 12. When the balloon expands, lobes are created as the balloon expands between the strips 66. It also contemplates combining the embodiments with FLEXINOL™ actuator wires, which are available from Dynalloy, Inc., for bifurcation applications.

Figure 13:
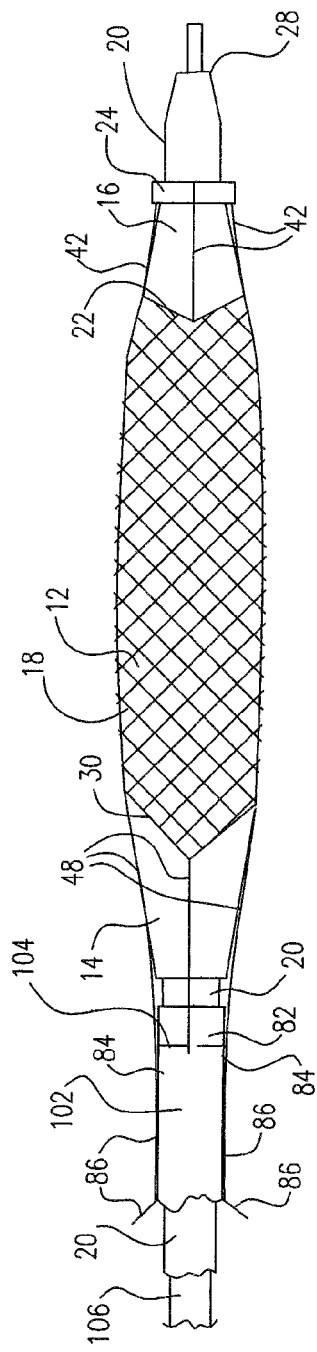
FIG. 13 is a side perspective view and partial cut-away of the distal portion of an embodiment of the invention.
Figure 14:
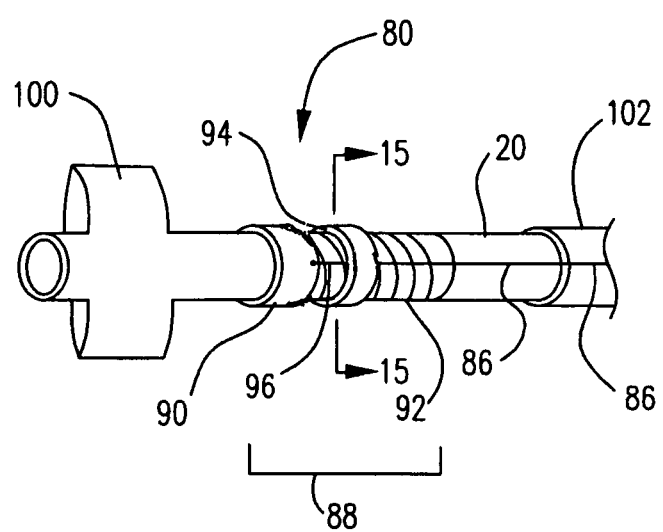
FIG. 14 is a side perspective view of the proximal portion of an embodiment of the invention.
Figure 15:
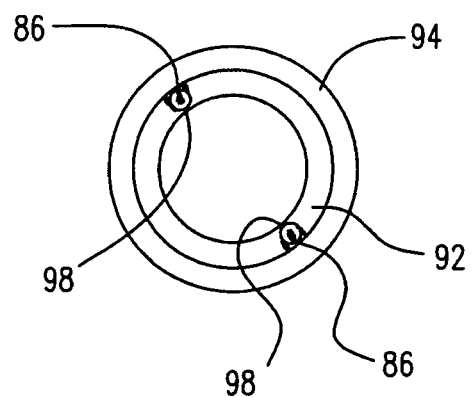
FIG. 15 is a cross-sectional view of the embodiment shown in FIG. 14 along lines 15-15.

FIGS. 13-15 illustrate a further embodiment of the invention. In this particular embodiment, a mesh restraining mechanism is used which may be controlled by the user via a catheter manifold 80, which is at the proximal end of the catheter system, as shown in FIG. 14.

In this particular embodiment, the proximal strands 48, which are connected to the distal end 30 of the mesh 18, are also connected to a sliding ring 82, which is slidable along the catheter shaft 20. The distal ends 84 of pull wires 86, one of which is partially shown in phantom, are also connected to the sliding ring 82. The pull wires 86 extend proximally to the manifold 80 and are connected to a retracting mechanism 88, which allows for manual retraction to apply a pulling force on the mesh 18 in order to draw the balloon 12 down after inflation.

As shown in FIGS. 14-15, in one particular embodiment, the retracting mechanism 88, shown on the catheter shaft 20 and adjacent to a hub 100, includes a sliding ring 90, a threaded portion 92 and a screw 94. The proximal end 96 of the pull wires 86 are connected to the sliding ring 82. As shown in FIG. 15, which a cross-section of the invention shown in FIG. 14 along lines 15-15, channels 98 are formed in the threaded portion 92 to provide space for the pull wires 86 to travel through between it and the screw 94. A longitudinal pulling force may be applied to the mesh 18 by winding the screw 94 proximately, thereby forcing the sliding ring 90 and pull wires 86 proximately. The reverse action may be taken to relieve the tension on the mesh 18 to allow the balloon 12 to be expanded.

The pull wires 86 may be embedded or attached to a tubular membrane 102. FIG. 13 shows a partial-cut away of the pull wire 86 and tubular membrane 102 combination. The tubular membrane 102 is a thin, flexible membrane, which keeps the pull wires 86 close to the catheter shaft 20 and prevents tangling. The distal end 104 of the tubular membrane 102 may be connected to the sliding ring 82 and extend proximally to a point near the manifold 80. The membrane 102 may act as part of the pull wires 86 and may extend further in the proximal direction than shown to the screw 94 and distally may be connected directly to the mesh 18. The membrane 102 may be made of any non-compliant material, including, but not limited to, nylons, PET, HDPE, etc.

Figure 21:
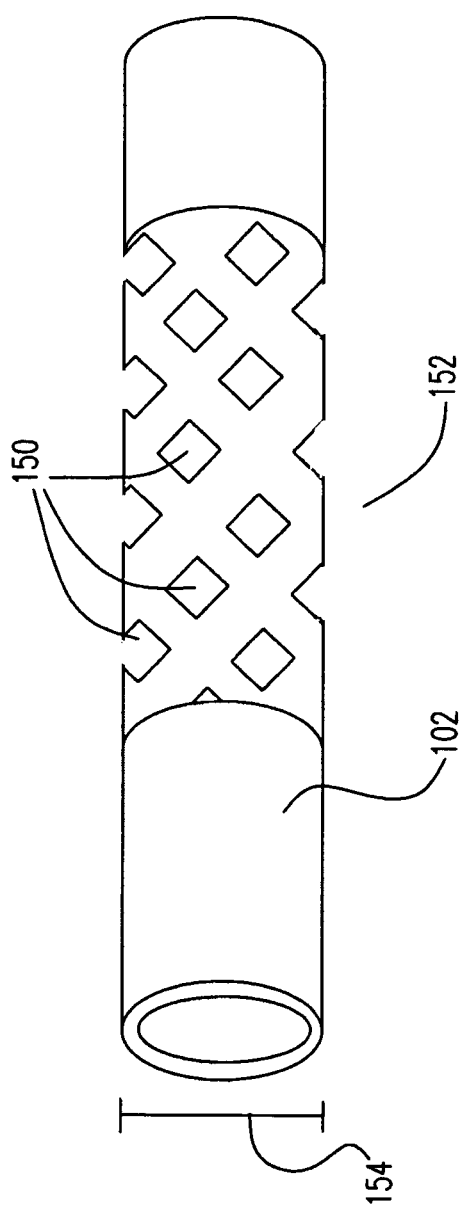
FIG. 21 is a perspective view of the distal portion of a membrane.
Figure 22:
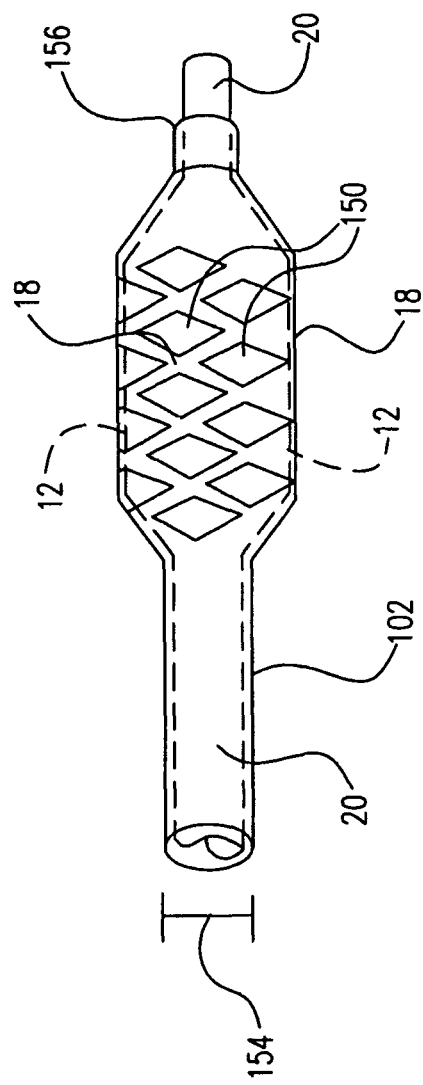
FIG. 22 is a side view of the distal portion of an embodiment of the invention, partially shown in phantom.

As shown in FIGS. 21-22, the membrane 102 may be integral with the mesh 18 by cutting a diamond pattern 150 in the distal portion 152 of the membrane. The diamond pattern 150 is placed over the balloon 12 to form the mesh 18. The diameter 154 of the membrane 102 is just large enough to slidably fit over the catheter shaft 20 and balloon 12, when the balloon 12 is in its contracted state. The diamond pattern 150 is cut into the membrane 102 when the membrane 102 is in its relaxed state. When the balloon 12 is inflated to its expanded state, the diamonds in the diamond pattern 150 change shape to accommodate the increase in diameter, as shown in FIG. 22. When pressure to the balloon 12 is reduced, the membrane 102 is drawn proximally, as described above, effectually drawing the balloon 12 down to its contracted state. Since the distal end 156 of the membrane 102 is not expanded with the balloon 12, it functions as an anchor during the drawing process.

In the embodiments shown, the mesh 18 is positioned about the balloon 12, but it is not connected to the balloon 12. However, as mentioned above, one end of the mesh 18 may be anchored to one of the waists 14, 16, of the balloon 12. The mesh controls and/or limits the expansion (diameter and length) of the balloon 12. It may cover a portion of the balloon 12 or part of it.

Figure 16:
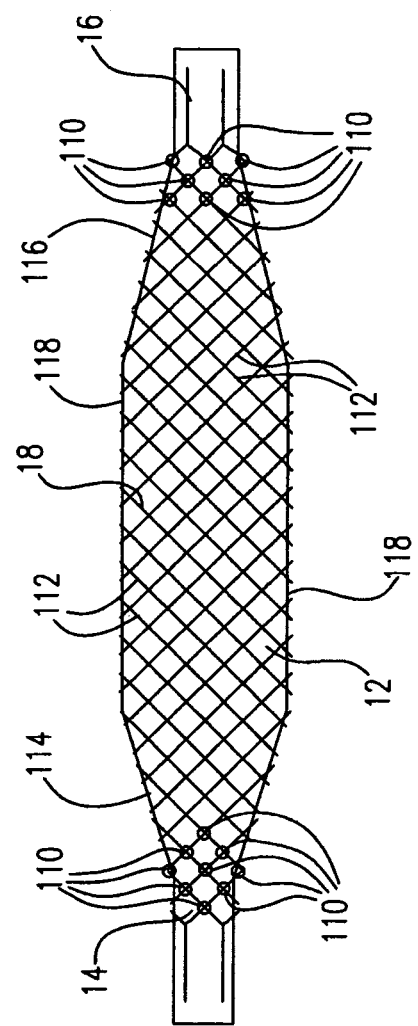
FIG. 16 is a side view of an embodiment of the mesh of the present invention mounted on a balloon.
Figure 17:
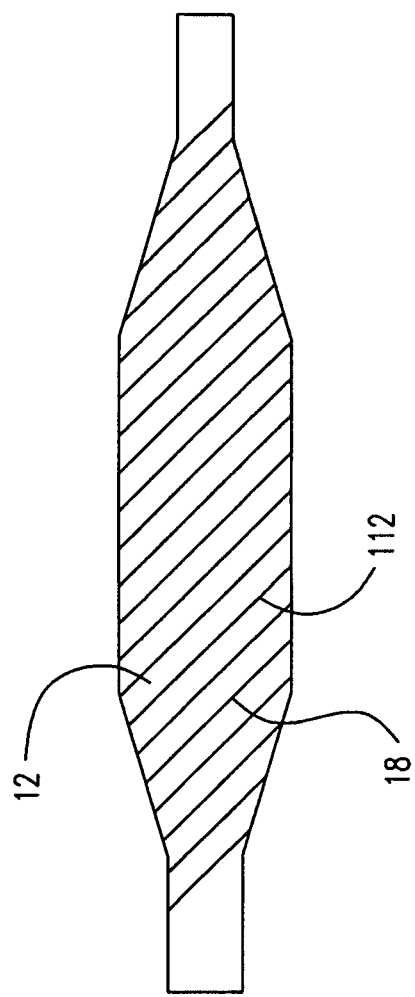
FIG. 17 is a side view of an embodiment of the mesh of the present invention mounted on a balloon.
Figure 18:
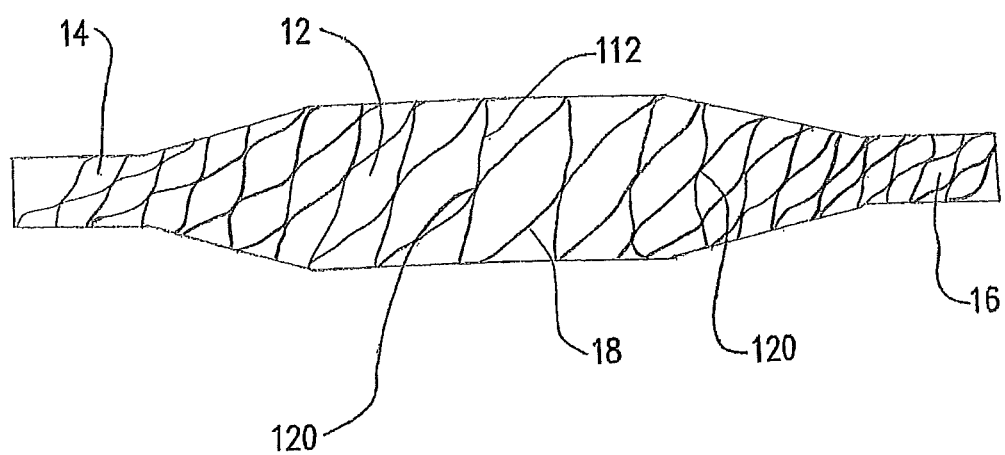
FIG. 18 is a side view of an embodiment of the mesh of the present invention mounted on a balloon.
Figure 19:
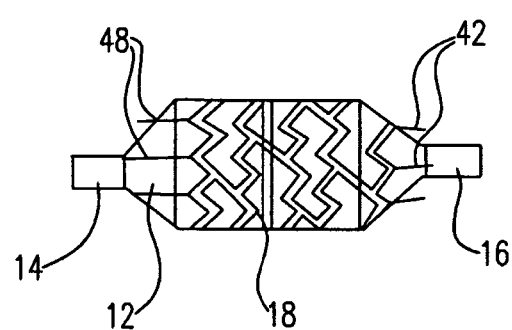
FIG. 19 is a side view of an embodiment of the mesh of the present invention mounted on a balloon.
Figure 20:
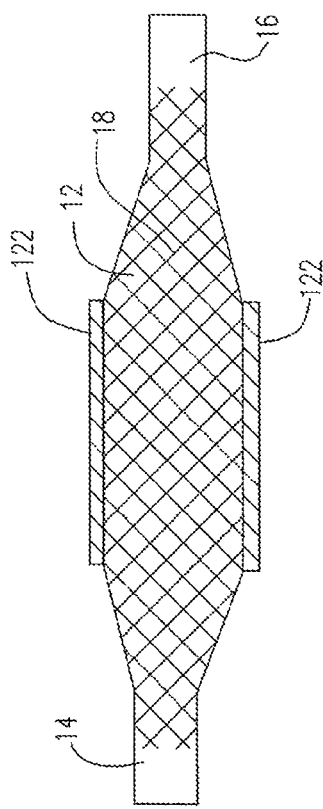
FIG. 20 is a side view of an embodiment of the mesh of the present invention mounted on a balloon with a cross-sectional view of a medical device mounted thereon.

FIGS. 16-19 illustrate particular placements and configurations of the mesh 18 on the balloon 12. As such, only the balloon 12 and mesh 18 are shown. The strands of the mesh 18 may be arranged to create the mesh 18 by known processes, such as, but not limited to, braiding, weaving, crocheting, etc. The distances between adjacent strands 112 may vary. The invention also contemplates a tight weave, wherein adjacent strands come in direct contact with one another. The mesh 18 may also take the form of, but not limited to, a coil as shown in FIG. 17, a coil, wherein adjacent strand portions 120 are joined, as shown in FIG. 18, or any random orientation, an example of which is shown in FIG. 19.

The present invention also contemplates using a mesh 18, as shown in FIG. 19, which is of one-piece construction. Multi-piece constructions are also contemplated. In this particular embodiment, a particular design or strand pattern is cut from a tube of material, or from a sheet of material, which is then rolled into a tube, using such techniques as found in implantable medical device making. Strands 42, 48, may be connected to the ends of the mesh 18 so as to control the extension of the one-piece mesh 18. When the balloon expands, mesh 18 expands with the balloon, foreshortening the length of the mesh. When the balloon expansion pressure is released, the mesh elongates as it is drawn down by axial pulling, as described above, collapsing the balloon. A mesh of this type can otherwise be used in the same manner as described in the other embodiments.

The mesh 18 of the various embodiments may take the shape of the expanded balloon 12 on which it is to be placed. In order to control the resulting shape of an expanded balloon, specific nodes 110, as shown in FIG. 16, are created. These nodes 110 are points where strands 112 of the mesh 18 cross each other and are connected to each other in a fixed manner. This may be achieved by adhesion, welding, or by some kind of mechanical mechanism, etc. The at least two strands 112 which make up each node 110 are fixed relative to one another at the point of the node 110. The remaining strands are allowed to move relative to one another as the mesh 18 is longitudinally and axially manipulated. It should be understood that the present invention is not limited to node 110 formations shown in the figures. The present invention contemplates any number of nodes 110 from zero nodes 110 to a node 110 at each strand cross-over point, both generally and specifically.

Linking specific cross-over-points to create nodes allows for the creation of specific features, such as waist 14, 16, to cone 114, 116, transitions or cone 114, 116, to body 118 transitions, wherein there is a decrease or increase in nodes from the waist(s) 14, 16, to the cone(s) 114, 116, and/or from the cone(s) 114, 116, to the body 118. Upon inflation of the balloon, the balloon comes in contact with the mesh. As expansion continues, the balloon portions, which come in contact with the pre-selected portions of the mesh 18 which have nodes 110, will have their movement and expansion restricted. Whereas, the balloon portions, which come in contact with the mesh 18 in places where nodes 110 are lacking and the strands of the mesh are allowed to move freely relative to each other, will have their movement and expansion less restricted. By pre-selecting the number and arrangement of the nodes 110, one may control the shape of the resulting expanded balloon 12. In this manner, the user may control the resulting diameter, both generally and regionally, and length of the expanded balloon.

Figure 23:
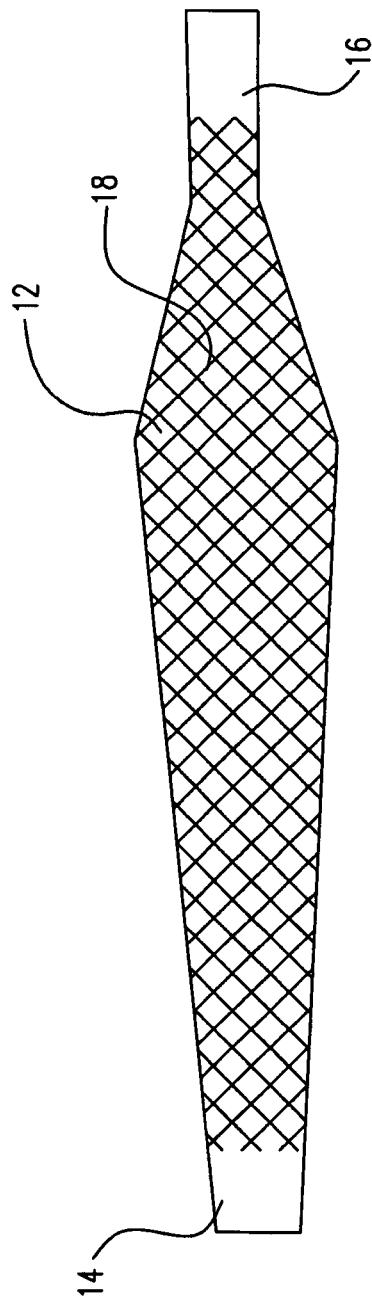
FIG. 23 is a side view of an embodiment of the mesh of the present invention mounted on a balloon.

As shown in FIG. 23, the mesh 18 may have a tapered shape, tapering either distally or proximally.

Figure 24:
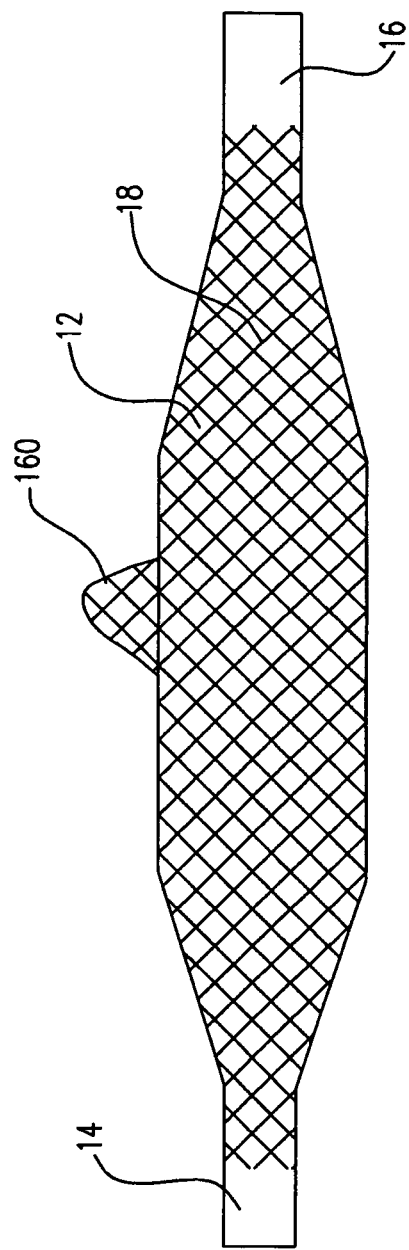
FIG. 24 is a side view of an embodiment of the mesh of the present invention mounted on a balloon.

As shown in FIG. 24, a mesh bulge 160 may be incorporated into the mesh 18 to accommodate a bifurcation balloon.

The mesh in the various embodiments may be made from strands that comprise high-strength inelastic fibers. By "inelastic", as used herein and in the appended claims, is meant that the fibers have very minimal elasticity or stretch under the stresses imposed during delivery, use and withdrawal of the device. In some embodiments the strands will have elongations of less than 10%, for instance 0.1 to 3% under these use conditions. High strength inelastic fibers useful in the present invention include, but are not limited to, high strength and/or ultra high molecular weight polyethylene, such as Spectra® or Dyneema® fibers; carbon fibers, ceramic fibers, such as Nextel™ fibers from 3M™; metal fibers, such as stainless steel fibers, i.e., Bekinox® VN continuous 1 micrometer diameter metal fibers from BEKAERT; aramid fibers for instance Kevlar®; fibers of liquid crystal polymers such as Vectan®; polyester fibers, for instance Dacron®, Terlon (PBT), Zylon (PBO), polyimide (PIM), etc. The fibers may be string-like or ribbon-like; that is, they have a flattened to a rectangular shape. The strands of the mesh may be composites of such fibers in a resin matrix or a mixture of different types of fibers in a single strand.

The present invention also contemplates a mesh having a predetermined arrangement of nodes mounted on a balloon, wherein the mesh is not attached to the balloon or catheter, but is free flowing over the balloon. The predetermined node arrangement allows the balloon to expand into a predetermined shape. In this particular embodiment, the mesh may have elastic characteristics to encourage the contraction of the balloon.

Figure 25:
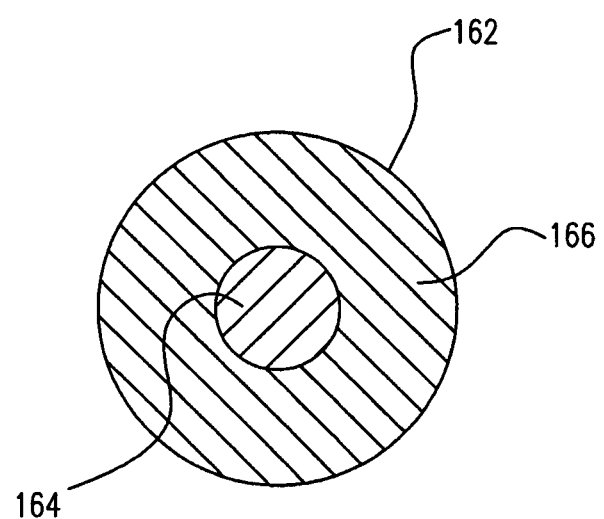
FIG. 25 is a cross-sectional view of a strand of an embodiment of the mesh of the present invention.
Figure 26:
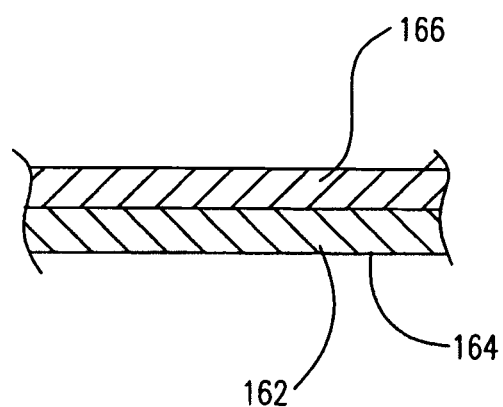
FIG. 26 is a cross-sectional view of a strand of an embodiment of the mesh of the present invention.

In some embodiments, the strands of the mesh 18 may be made of two or more types of material. As shown in FIGS. 25 and 26, the strands 162 may be a combination of plastic deforming strands (PDS) 164 and elastic strands (ES) 166. The strands 162 may be multi-layered, as shown in FIG. 26, which shows a longitudinal strand 166 cross-section, or one material may be enclosed within the other, as shown in FIG. 25, which is a circumferential cross-section of a strand 166. The elastic strand 166 may also be within the plastic deforming strand 164.

Figure 27:
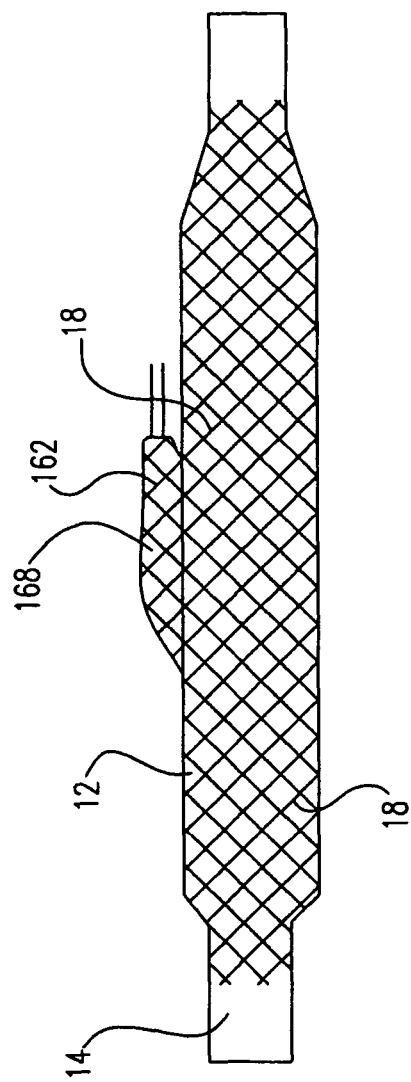
FIG. 27 is a side view of an embodiment of the mesh of the present invention mounted on a balloon.

FIGS. 27-28 illustrate a mesh 18 made from the PDS/ES combination strands 162 about a balloon 12 having a bifurcation balloon branch 168. As shown in FIG. 27, the elastic nature of the strands 162 holds the branch 168 down to allow for insertion of the catheter into the body. Upon activation of the balloon branch 168, the applied force stretches the strands 162. Afterwards, the balloon branch 168 is pulled back into place by the elastic strands 166.

In some embodiments, the mesh 18 may have a coating of light curable ceramics and be cured to varying levels down the length of the shaft of the catheter. This would allow for an elastic shaft over the entire length and allow for balloon expansion via non-coated-cured section(s). Braid pitch of the mesh 18 and the level of cure can control pushability and trackability. Portions of the catheters and other medical devices may thereby be selectively stiffened, as desired, to alter the pushability and trackability. For examples selective portions of the catheter shaft may be coated and cured to different extents. Curable coating methods and materials may be found in U.S. Patent Application Publication No. 20050033407 A1, which is incorporated herein by reference in its entirety.

The embodiments of the present invention may also, as mentioned above, be incorporated into bifurcated catheter assemblies. Examples of systems that address vessel bifurcation are shown and described in:

U.S. patent application Ser. No. 10/375,689, filed Feb. 27, 2003 and U.S. patent application Ser. No. 10/657,472, filed Sep. 8, 2003 both of which are entitled Rotating Balloon Expandable Sheath Bifurcation Delivery; U.S. patent application Ser. No. 10/747,546, filed Dec. 29, 2003 and entitled Rotating Balloon Expandable Sheath Bifurcation Delivery System; U.S. patent application Ser. No. 10/757,646, filed Jan. 13, 2004 and entitled Bifurcated Stent Delivery System; and U.S. patent application Ser. No. 10/784,337, filed Feb. 23, 2004 and entitled Apparatus and Method for Crimping a Stent Assembly; the entire content of each of which are incorporated herein by reference.

Embodiments of the present invention can be incorporated into those shown and described in the various references cited above. Likewise, embodiments of the inventions shown and described therein can be incorporated herein.

In some embodiments the mesh 18 may include one or more therapeutic and/or lubricious coatings applied thereto. In some embodiments the agent is placed on the mesh in the form of a coating. In at least one embodiment the coating includes at least one therapeutic agent and at least one polymer agent. A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the agent may be a polystyrene-polyisobutylene-polystyrene triblock copolymer (SIBS), polyethylene oxide, silicone rubber and/or any other suitable substrate.

The balloon 12 may be a compliant or non-compliant balloon and may be made from suitable materials used in the art, such as, but not limited to, conventional polymers and copolymers used in medical balloon construction, such as, but not limited to, polyethylene, polyethylene terephthalate (PET), polycaprolactam, polyesters, polyethers, polyamides, polyurethanes, polyimides, ABS copolymers, polyester/polyether block copolymers, ionomer resins, liquid crystal polymers, and rigid rod polymers.

The invention also contemplates that a medical device 122 may be carried on the balloon for delivery to a target site in the body. Contemplated medical devices included, but are not limited to, stents, grafts, stent-grafts, vena cava filters, vascular implants, and similar implantable medical devices. These medical devices are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, such as a nitinol shape memory stent, mechanically expandable, such as a balloon expandable stent, or hybrid expandable. In the particular embodiments described above, the medical device 122 would be mounted on the balloon, such that the mesh 18 is between the medical device 122 and the balloon 12.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A medical device comprising:
a catheter shaft having a distal portion and a proximal portion;
an expandable member mounted on the distal portion of the catheter shaft, the expandable member comprising a distal end portion, a proximal end portion and a central portion positioned between the distal end portion and the proximal end portion, the expandable member having an expanded state and a contracted state and being expandable from its contracted state to its expanded state;
a mesh member comprising a plurality of strands forming a mesh wherein the individual strands of the mesh cross other strands of the mesh, the mesh member surrounding the expandable member, having a first end and a second end, and being substantially free-floating over the expandable member, the mesh member being in the shape of a spiral having a single chirality, the mesh having an inner surface facing the catheter shaft, the inner surface being the entirety of the mesh that is facing the catheter shaft, wherein, when the expandable member is in its expanded state, the inner surface of the mesh at its greatest distance from the catheter shaft is disposed radially around the expandable member and the entirety of the inner surface of the mesh being in contact with and urged against the expandable member; and
a restraining mechanism associated with the mesh member, wherein the restraining mechanism continuously applies a longitudinal biasing force on the mesh member when the expandable member is in its expanded state, the restraining mechanism having a first end fixed to the catheter shaft and second end connected to the first end of the mesh member, wherein the second end of the restraining mechanism and the first end of the mesh member are movable in a longitudinal direction relative to the catheter shaft and the first end of the restraining mechanism.

2. The medical device of claim 1, wherein the second end of the mesh member is fixed relative to the catheter shaft.

3. The medical device of claim 1, wherein the restraining mechanism comprises an elastic member, such that, when the expandable member is in its expanded state, the elastic member is stretched and exerts a longitudinal force on the mesh member.

4. The medical device of claim 1, wherein the individual strands of the mesh cross other strands of the mesh at first and second junctures,
at the first junctures the crossing strands are fixed, and
at the second junctures the crossing strands are free to slide relative to each other.

5. The medical device of claim 4, the expandable member being a medical balloon, the medical balloon having a proximal cone, a distal cone and a body portion between the proximal and distal cones, wherein, when the balloon is inflated, the first junctures of the mesh are positioned over at least one annular transition zone where one of the proximal or distal cones joins the body portion of the balloon.

6. The medical device of claim 4, wherein the expandable member is a medical balloon, the medical balloon having a proximal cone, a distal cone and a body portion between the proximal and distal cones, wherein the first junctures of the mesh are positioned over at least one of the proximal and distal cones when the balloon is inflated.

7. The medical device of claim 1, wherein the strands of the mesh member comprise an inelastic material.

8. The medical device of claim 1, wherein the restraining mechanism comprises a loadable spring, a portion of the loadable spring being fixed relative to the catheter shaft and a portion of the loadable spring being connected to and longitudinally with the first end of the mesh member, wherein, when the expandable member is in its expanded state, the loadable spring takes on a load and applies a longitudinal force on the mesh member.

9. The medical device of claim 1, wherein an implantable medical device is mounted on the expandable member, such that the mesh is between the medical device and the expandable member.

10. The medical device of claim 9, wherein the implantable medical device is a stent.

11. The medical device of claim 1, wherein the mesh is of one-piece construction.

12. The medical device of claim 1 wherein the mesh expands in tandem with and upon the application of pressure by the expandable member upon the expandable member's expansion from its contracted state to its expanded state, such that the mesh is in constant reliance upon direct outward pressure from the expandable member to the inner surface of the mesh by the expansion of the expandable member to expand and to maintain an expanded state.

13. The medical device of claim 1, the expandable member being a medical balloon, wherein a radial cross-sectional center plane bisects the medical balloon and a radial cross-sectional center plane bisects the mesh, the radial cross-sectional center plane of the medical balloon and the radial cross-sectional center plane of the mesh being radially in alignment.

14. A medical device comprising:
a catheter shaft having a distal portion and a proximal portion;
an expandable member mounted on the distal portion of the catheter shaft, the expandable member comprising a distal end portion, a proximal end portion and a central portion positioned between the distal end portion and the proximal end portion, the expandable member having an expanded state and a contracted state and being expandable from its contracted state to its expanded state;
a mesh member comprising a plurality of strands forming a mesh wherein the individual strands of the mesh cross other strands of the mesh, the mesh member surrounding the expandable member, having a proximal end and a distal end, and being substantially free-floating over the expandable member, the mesh member being in the shape of a left-handed or a right-handed spiral, the mesh having an inner surface facing the catheter shaft, the inner surface being the entirety of the mesh that is facing the catheter shaft, wherein, when the expandable member is in its expanded state, the inner surface of the mesh at its greatest distance from the catheter shaft is disposed radially around the expandable member and the entirety of the inner surface of the mesh being in contact with and urged against the expandable member; and
a restraining mechanism associated with the mesh member, wherein the restraining mechanism continuously applies a biasing force on the mesh member when the expandable member is in its expanded state, the restraining mechanism comprising a first strip, the first strip having a proximal end and a distal end, wherein the proximal and distal ends of the first strip are connected to the catheter shaft and wherein at least one of the ends of the first strip is slidably connected to the catheter shaft in a longitudinal direction, the first strip extending longitudinally across the expandable member.

15. The medical device of claim 14, wherein the first strip is connected to the mesh member and applies a collapsing force on the expandable member, when the expandable member is in its expanded state.

16. The medical device of claim 15, wherein the first strip is embedded in the mesh member material.

17. The medical device of claim 14, the restraining mechanism further comprising a second strip, the second strip having a proximal end and a distal end, wherein the proximal and distal ends of the second strip are connected to the catheter shaft and wherein the second strip extends longitudinally across the expandable member.

18. A medical device comprising:
a catheter shaft having a distal portion and a proximal portion;
an expandable member mounted on the distal portion of the catheter shaft, the expandable member comprising a distal end portion, a proximal end portion and a central portion positioned between the distal end portion and the proximal end portion, the expandable member having an expanded state and a contracted state and being expandable from its contracted state to its expanded state;
a mesh member comprising a plurality of strands forming a mesh that has a length and that has a width extending between two lengthwise edges wherein the individual strands of the mesh cross other strands of the mesh, the mesh member surrounding the expandable member, having a proximal end and a distal end, and being substantially free-floating over the expandable member, the mesh member extending lengthwise in the shape of a single spiral, the mesh having an inner surface facing the catheter shaft, the inner surface being the entirety of the mesh that is facing the catheter shaft, wherein, when the expandable member is in its expanded state, the inner surface of the mesh at its greatest distance from the catheter shaft is disposed radially around the expandable member and the entirety of the inner surface of the mesh being in contact with and urged against the expandable member;
a manifold situated at the proximal portion of the catheter shaft; and
a restraining mechanism associated with the mesh member, wherein the restraining mechanism applies a longitudinal force on the mesh member when the expandable member is in its expanded state, the restraining mechanism comprising a sliding member slidably mounted on the catheter shaft, wherein the proximal end of the mesh member is connected to the sliding member, the restraining mechanism further comprising a retracting mechanism, wherein the retracting mechanism retracts the sliding member proximally, resulting in a longitudinal force on the mesh member, the retracting mechanism comprising a pull back mechanism, the pull back mechanism being connected to the sliding member and being controllable from the manifold, wherein the pull back mechanism comprises a plurality of pull wires, the plurality of pull wires being connected to the sliding member and extending proximately to the manifold.

19. The medical device of claim 18, wherein the pull wires are connected to a tubular membrane over a substantial portion of their length.

20. The medical device of claim 18 wherein the mesh expands in tandem with and upon the application of pressure by the expandable member upon the expandable member's expansion from its contracted state to its expanded state, such that the mesh is in constant reliance upon direct outward pressure from the expandable member to the inner surface of the mesh by the expansion of the expandable member to expand and to maintain an expanded state.

21. The medical device of claim 18, the expandable member being a medical balloon, wherein a radial cross-sectional center plane bisects the medical balloon and a radial cross-sectional center plane bisects the mesh, the radial cross-sectional center plane of the medical balloon and the radial cross-sectional center plane of the mesh being radially in alignment.

22. A medical device comprising:
a catheter shaft having a distal portion and a proximal portion;
an expandable member, the expandable member being mounted on the distal portion of the catheter shaft, the expandable member comprising a distal end portion, a proximal end portion and a central portion positioned between the distal end portion and the proximal end portion, the expandable member having an expanded state and a contracted state, and being expandable from its contracted state to its expanded state; and
a mesh member comprising a plurality of strands forming a mesh wherein the individual strands of the mesh cross other strands of the mesh, the mesh member surrounding the expandable member, having a proximal end and a distal end, and being substantially free-floating over the expandable member, the mesh member being in the shape of a spiral, the mesh having an inner surface facing the catheter shaft, the inner surface being the entirety of the mesh that is facing the catheter shaft, wherein, when the expandable member is in its expanded state, the inner surface of the mesh at its greatest distance from the catheter shaft is disposed radially around the expandable member and the entirety of the inner surface of the mesh being in contact with and urged against the expandable member;
wherein all of the strands extending from the proximal end of the mesh member to the distal end of the mesh member have a common chirality.

23. The medical device of claim 22, wherein the mesh comprises an inelastic material.

24. A medical device comprising:
a catheter shaft having a distal portion and a proximal portion;
an expandable member mounted on the distal portion of the catheter shaft, the expandable member comprising a distal end portion, a proximal end portion and a central portion positioned between the distal end portion and the proximal end portion, the expandable member having an expanded state and a contracted state and being expandable from its contracted state to its expanded state; and
a mesh member comprising a plurality of strands forming a mesh that has a length and that has a width between first and second lengthwise mesh edges wherein the individual strands of the mesh cross other strands of the mesh, the mesh member surrounding the expandable member, having a proximal end and a distal end, and being substantially free-floating over the expandable member, the mesh member being in the shape of a spiral that has a pitch wherein a seam is formed by joining the first and second lengthwise mesh edges, each strand comprising a plastic deforming strand and an elastic strand, the mesh having an inner surface facing the catheter shaft, the inner surface being the entirety of the mesh that is facing the catheter shaft, wherein, when the expandable member is in its expanded state, the inner surface of the mesh at its greatest distance from the catheter shaft is disposed radially around the expandable member and the entirety of the inner surface of the mesh being in contact with and urged against the expandable member.

* * * * *